US012635926B2

(12) United States Patent
Kwon et al.

(10) Patent No.: US 12,635,926 B2
(45) Date of Patent: May 26, 2026

(54) APPARATUS USING TWO LEAD ASYNCHRONOUS ELECTROCARDIOGRAMS

(71) Applicant: MEDICAL AI CO., LTD., Seoul (KR)

(72) Inventors: Joon Myoung Kwon, Seoul (KR);
Yong-Yeon Jo, Seoul (KR)

(73) Assignee: MEDICAL AI CO., LTD., Seoul (KR)

( * ) Notice: Subject to any disclaimer, the term of this patent is extended or adjusted under 35 U.S.C. 154(b) by 102 days.

(21) Appl. No.: 18/558,526

(22) PCT Filed: Aug. 17, 2022

(86) PCT No.: PCT/KR2022/012277
§ 371 (c)(1),
(2) Date: Nov. 1, 2023

(87) PCT Pub. No.: WO2023/022507
PCT Pub. Date: Feb. 23, 2023

(65) Prior Publication Data
US 2024/0225514 A1     Jul. 11, 2024

(30) Foreign Application Priority Data

Aug. 17, 2021    (KR) ......................... 10-2021-0107772

(51) Int. Cl.
*A61B 5/327*     (2021.01)
*A61B 5/00*      (2006.01)
*G16H 50/20*     (2018.01)

(52) U.S. Cl.
CPC ............ *A61B 5/327* (2021.01); *A61B 5/0006* (2013.01); *A61B 5/002* (2013.01); *G16H 50/20* (2018.01)

(58) Field of Classification Search
CPC ....... A61B 5/327; A61B 5/0003; A61B 5/002; A61B 5/28; A61B 5/318; A61B 5/346;
(Continued)

(56) References Cited

U.S. PATENT DOCUMENTS

2021/0121117 A1     4/2021    Albert
2021/0169392 A1     6/2021    Albert

FOREIGN PATENT DOCUMENTS

CN     112932499 A     6/2021
JP     2021-81915 A    5/2021
(Continued)

OTHER PUBLICATIONS

Yong-Yeon Jo et al: "ECGT2T: Electrocardiogram synthesis from Two asynchronous leads to Ten leads", arxiv.org, Cornell University Library, 201 Olin Library Cornell University Ithaca, NY 14853, Feb. 28, 2021 (Feb. 28, 2021), XP081892939, (Year: 2021).*
(Continued)

*Primary Examiner* — Boniface N Nganga
(74) *Attorney, Agent, or Firm* — Perkins Coie LLP

(57) ABSTRACT

The present invention relates to a method for generating synchronous electrocardiograms based on two lead asynchronous electrocardiograms. According to the present invention, there is provided a method of generating synchronous electrocardiograms, the method including: collecting electrocardiogram data of a plurality of patients from a server operated by a hospital, and classifying the collected electrocardiogram data by style; constructing a deep learning algorithm, and training a constructed machine learning model on styles of electrocardiograms by inputting the classified electrocardiogram data into the constructed machine learning model; acquiring two lead electrocardiograms, measured at different times, using electrodes installed on the body of a measurement subject; and generating a plurality of virtual synchronous lead electrocardiograms by inputting the lead electrocardiograms of the measurement subject to the trained machine learning model.

20 Claims, 6 Drawing Sheets

(58) Field of Classification Search
CPC ..... A61B 5/349; A61B 5/7267; A61B 5/7275;
A61B 5/7278; G16H 50/20
See application file for complete search history.

(56) References Cited

FOREIGN PATENT DOCUMENTS

| | | | |
|---|---|---|---|
| JP | 33101965 | A | 7/2021 |
| KR | 1020150044311 | A | 4/2015 |
| KR | 1020160064607 | A | 6/2016 |
| KR | 102008196 | B1 | 8/2019 |
| KR | 102078703 | B1 | 2/2020 |
| KR | 102093257 | B1 | 3/2020 |
| KR | 1020200068161 | A | 6/2020 |
| KR | 102142841 | B1 | 8/2020 |
| KR | 1020220040516 | A | 3/2022 |
| WO | 2021015570 | A1 | 1/2021 |

OTHER PUBLICATIONS

Yong-Yeon Jo et al: "Electrocardiogram synthesis", arxiv.org, Cornell
University Library, 201 Olin Library Cornell University Ithaca, NY
14853, Jun. 3, 2021 (Jun. 3, 2021), XP081979356, (Year: 2021).*

* cited by examiner

FIG. 1     100

DATA CLASSIFICATION UNIT ~110

TRAINING UNIT ~120

ELECTROCARDIOGRAM ACQUISITION UNIT ~130

ELECTROCARDIOGRAM GENERATION UNIT ~140

VAE
Variational Auto Encoder

APPARATUS USING TWO LEAD ASYNCHRONOUS ELECTROCARDIOGRAMS

CROSS REFERENCE TO RELATED APPLICATION(S)

This application is a National Stage of International Application No. PCT/KR2022/012277 filed on Aug. 17, 2022, claiming priority based on Korean Patent Application No. 10-2021-0107772 filed on Aug. 17, 2021, the disclosures of which are incorporated herein by reference in their entireties.

TECHNICAL FIELD

The present invention relates to a method for generating synchronous electrocardiograms based on two lead asynchronous electrocardiograms, and more specifically to a method for generating synchronous electrocardiogram information from two pieces of lead asynchronous electrocardiogram information, measured at different times, using a deep learning algorithm.

BACKGROUND ART

An electrocardiogram is a graphical record of electrical potentials related to heartbeat on the surface of the human body. Such electrocardiograms include not only standard 12-lead electrocardiograms but also exercise stress electrocardiograms and Holter electrocardiograms. Electrocardiograms are used for the examination and diagnosis of circulatory diseases, and have the advantages of being simple, relatively inexpensive, non-invasive, and easily recorded repeatedly.

As for a standard 12-lead electrocardiogram used in hospitals, six electrodes are attached to the front of the chest, three electrodes (four electrodes when a ground electrode is included) are attached to the limbs, 12-lead information is all collected and combined, and then a disease is diagnosed. A 12-lead electrocardiogram records electrical potentials of the heart in 12 electrical directions centered on the heart. Through this, the disease of the heart confined to one area can be accurately diagnosed.

However, it is difficult to measure a 12-lead electrocardiogram at home or in everyday life because the chest must be exposed to attach chest electrodes to take a 12-lead electrocardiogram and it is difficult for the general public to attach nine electrodes (three limb electrodes and six chest electrodes) to correct locations. In addition, it is difficult to use a 12-lead electrocardiogram for real-time monitoring because it is difficult to move after the attachment of ten electrodes.

Recently, there has been proposed a technology for measuring the side leads of a plurality of electrocardiograms using a 1-lead electrocardiogram device such as a smart watch. However, when electrocardiograms are measured using the 1-lead electrocardiogram device, a problem arises in that the accurate state of the heart cannot be determined because the electrocardiograms are not measured at the same time.

A background technology of the present invention is disclosed in Korean Patent Application Publication No. 10-2015-0044311 (published on Apr. 24, 2015).

DISCLOSURE

Technical Problem

As described above, the present invention is intended to provide a method for generating synchronous electrocardiogram information from two pieces of lead asynchronous electrocardiogram information, measured at different times, using a deep learning algorithm.

Technical Solution

According to an embodiment of the present invention for solving the above technical problem, there is provided a method of generating synchronous electrocardiograms using a synchronous electrocardiogram generation apparatus, the method including: collecting electrocardiogram data of a plurality of patients from a server operated by a hospital, and classifying the collected electrocardiogram data by style; constructing a deep learning algorithm, and training a constructed machine learning model on styles of electrocardiograms by inputting the classified electrocardiogram data into the constructed machine learning model; acquiring two lead electrocardiograms, measured at different times, using electrodes installed on the body of a measurement subject; and generating a plurality of virtual synchronous lead electrocardiograms by inputting the lead electrocardiograms of the measurement subject to the trained machine learning model.

Classifying the collected electrocardiogram data by style may include classifying a plurality of the collected electrocardiogram data by at least one style among gender, age, disease status, attachment positions of electrodes, waveform characteristics, waveform curves, and noise signals of each patient.

Training a constructed machine learning model on styles of electrocardiograms may include training the machine learning model on the correlations between a plurality of electrocardiogram data and electrocardiogram styles by inputting the plurality of electrocardiogram data and the electrocardiogram styles to the machine learning model.

Training a constructed machine learning model on styles of electrocardiograms may include constructing 12 machine learning models to perform training on styles for 12 standard electrocardiograms.

The 12 machine learning models may be constructed using one principle selected between an autoencoder and a generative adversarial network, or may be constructed using a mixture of the two principles.

Generating a plurality of virtual synchronous lead electrocardiograms may include generating 12 pieces of electrocardiogram data changed into each style by inputting the lead electrocardiograms of the measurement subject into the 12 machine learning models.

Advantageous Effects

As described above, according to the present invention, synchronous electrocardiogram information is generated from two pieces of lead asynchronous electrocardiogram information using a deep learning algorithm, so that there can be provided highly accurate electrocardiograms that are not influenced by the age, gender, disease status, and attachment positions of electrodes of a measurement subject.

MODE FOR INVENTION

Figure 1:
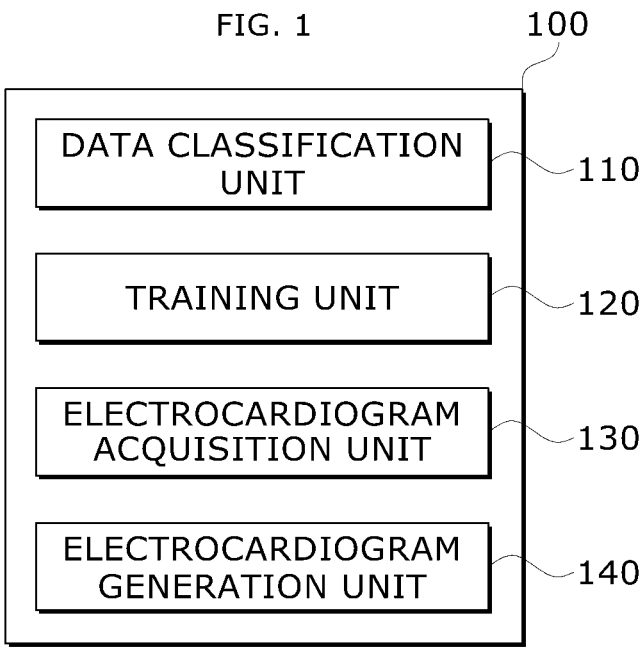
FIG. 1 is a block diagram of a synchronous electrocardiogram generation apparatus according to an embodiment of the present invention.

Preferred embodiments according to the present invention will be described in detail below with reference to the accompanying drawings. In this process, the thicknesses of lines or sizes of components shown in the drawings may be shown exaggerated for clarity and convenience of description.

Additionally, the terms to be described below are terms defined by taking into consideration the functions thereof in the present invention, and may vary depending on the intention or custom of a user or operator. Accordingly, the definitions of these terms should be made based on the content throughout the present specification.

A synchronous electrocardiogram generation apparatus according to an embodiment of the present invention will be described in more detail below using FIG. 1.

FIG. 1 is a block diagram of a synchronous electrocardiogram generation apparatus according to an embodiment of the present invention.

As shown in FIG. 1, a synchronous electrocardiogram generation apparatus 100 according to an embodiment of the present invention includes a data classification unit 110, a training unit 120, an electrocardiogram acquisition unit 130, and an electrocardiogram generation unit 140.

The data classification unit 110 collects standard 12-lead electrocardiogram data from a hospital server, and classifies the collected electrocardiogram data by style.

The training unit 120 constructs a machine learning model, and trains the machine learning model to generate synchronous electrocardiograms by inputting a plurality of pieces of classified electrocardiogram data to the constructed machine learning model.

The electrocardiogram acquisition unit 130 acquires one or two pieces of lead electrocardiogram data from a measurement subject.

Finally, the electrocardiogram generation unit 140 generates a plurality of synchronous electrocardiograms by inputting the one or two pieces of lead electrocardiogram data to the trained machine learning model.

A method for generating synchronous electrocardiograms using the synchronous electrocardiogram generation apparatus 100 according to an embodiment of the present invention will be described in more detail below using FIGS. 2 to 6.

Figure 2:
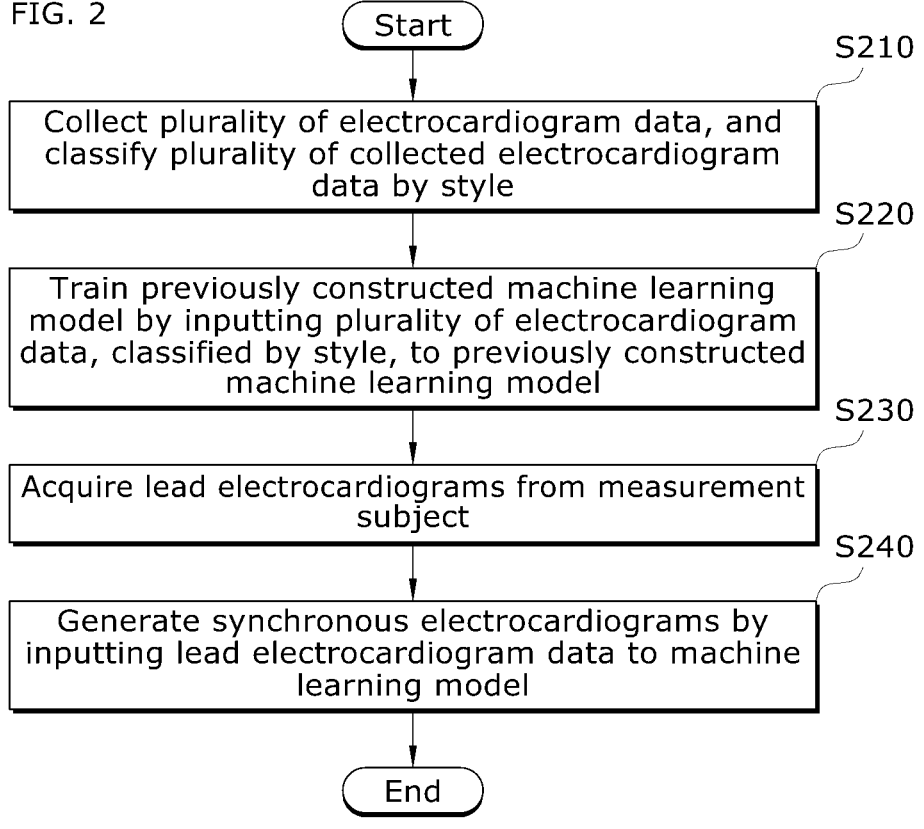
FIG. 2 is a flowchart illustrating a method for generating synchronous electrocardiograms using a synchronous electrocardiogram generation apparatus according to an embodiment of the present invention.

FIG. 2 is a flowchart illustrating a method for generating synchronous electrocardiograms using a synchronous electrocardiogram generation apparatus according to an embodiment of the present invention.

As shown in FIG. 2, the synchronous electrocardiogram generation apparatus 100 according to an embodiment of the present invention collects a plurality of pieces of electrocardiogram server, and data from a hospital classifies the plurality of pieces of collected electrocardiogram data by style in step S210.

More specifically, the data classification unit 110 collects standard 12-lead electrocardiograms. In this case, the standard 12-lead electrocardiograms refer to the electrocardiograms measured from electrodes attached to the human bodies of normal people and heart disease patients.

The data classification unit 110 classifies the plurality of collected standard 12-lead electrocardiograms by style. In this case, the style includes at least one of the gender, age, disease status, attachment positions of electrodes, waveform characteristics, waveform curves, and noise signals of each patient.

In more detail, each lead electrocardiogram has its own style. This includes not only the characteristics of the P, Q, R, S, or T waveform specified by existing medical knowledge, but also parts such as curves or noise signals that cannot be specified by existing medical knowledge.

Furthermore, the style of each lead electrocardiogram is influenced by the characteristics of a measurement subject. For example, the age and gender of a measurement subject influences the style of each lead electrocardiogram. In the case of the elderly, the heart muscle decreases, so that there is a tendency for the amplitude of the electrocardiogram to decrease. In the case of women, due to the breasts, the positions of electrocardiogram electrodes for measurement may be lowered or the distances between the heart and the electrodes may increase, causing deformation in the shape of an electrocardiogram.

Additionally, the style of each lead electrocardiogram is influenced by the disease of a measured person. In the case of chronic lung disease (chronic obstructive pulmonary disease), as the capacity of the lungs increases, the heart between the lungs is erected vertically, causing the electrical flow of the heart to change vertically in three-dimensional space.

Furthermore, the style of each lead electrocardiogram is also influenced by the attachment location of a corresponding electrode. For example, in the case of an I-lead electrocardiogram for which electrodes are attached to both arms and the potential difference between the two electrodes is used, there may be a difference between the case of performing measurement by attaching electrodes to both wrists and the case of performing measurement by attaching electrodes to both shoulders.

Therefore, in an embodiment of the present invention, a plurality of pieces of electrocardiogram data are classified by style.

When step S210 is completed, the training unit 120 trains a previously constructed machine learning model by inputting the plurality of pieces of electrocardiogram data, classified by style, to the previously constructed machine learning model in step S220.

First, the training unit 120 constructs a machine learning model. In this case, a plurality of machine learning models may be constructed according to the types of lead electrocardiograms. That is, the training unit 120 constructs 12 machine learning models. For example, in order to generate a V1-lead electrocardiogram, the training unit 120 constructs a machine learning model that learns a V1-lead style based on a large amount of V1-lead electrocardiogram data.

Meanwhile, machine learning models may be constructed using a principle selected between an autoencoder and a generative adversarial network, or may be constructed using a mixture of the two principles.

Figure 3:
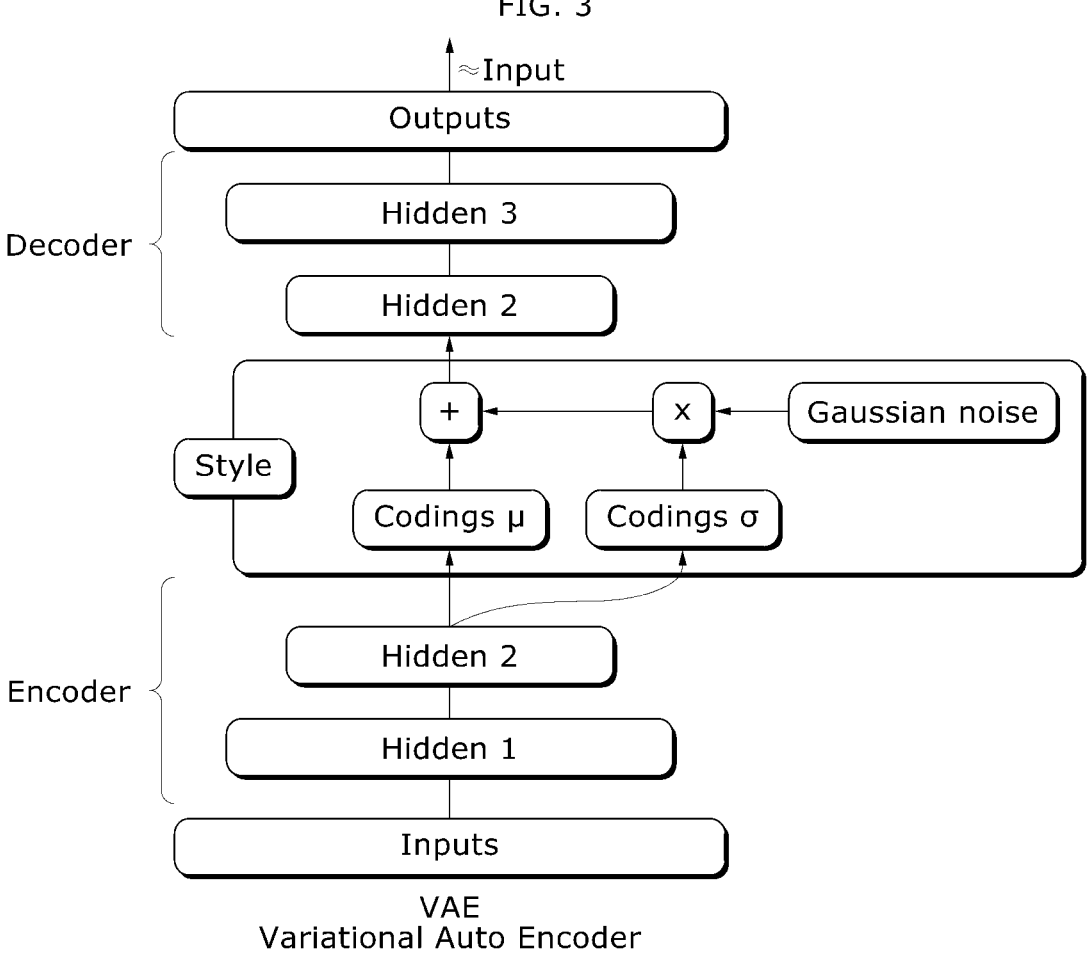
FIG. 3 is an example diagram illustrating a machine learning model constructed based on the principle of an autoencoder.

FIG. 3 is an example diagram illustrating a machine learning model constructed based on the principle of an autoencoder.

As shown in FIG. 3, the machine learning model constructed on the autoencoder principle includes an encoder configured to express the potential characteristics of data and a decoder configured to restore corresponding expressions to original data.

Figure 4:
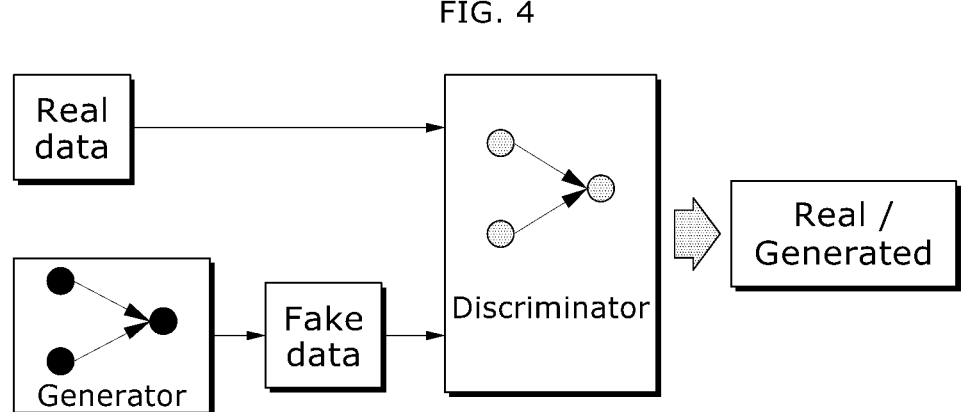
FIG. 4 is an example diagram illustrating a machine learning model constructed based on the principle of a generative adversarial network.

FIG. 4 is an example diagram illustrating a machine learning model constructed based on the principle of a generative adversarial network.

As shown in FIG. 4, the machine learning model constructed based on the principle of a generative adversarial network includes a generator and a discriminator. The generator generates synthetic electrocardiogram data by inputting randomly generated variables, and the discriminator classifies synthetic electrocardiogram data and real data as generated or real.

However, a basic generative adversarial network has a problem in that it is difficult to generate a specific lead electrocardiogram. Accordingly, in an embodiment of the present invention, the generator is changed into an autoencoder type. In other words, a machine learning model according to an embodiment of the present invention may be constructed using a mixture of the principles of a generative adversarial network and an autoencoder.

After the machine learning model has been constructed, the training unit 120 trains the machine learning model on the correlations between collected electrocardiogram data and corresponding styles by inputting the electrocardiogram data and the electrocardiogram styles to the machine learning model.

In the state in which step S220 is completed, the electrocardiogram acquisition unit 130 acquires lead electrocardiograms from the measurement subject in step S230.

More specifically, a measurement subject measures electrocardiograms through a 1-lead electrocardiogram device (not shown) such as a smart watch. That is, the electrocardiogram acquisition unit 130 acquires one or two pieces of lead electrocardiogram data from the 1-lead electrocardiogram device.

Thereafter, the electrocardiogram generation unit 140 generates synchronous electrocardiograms by inputting the acquired one or two pieces of lead electrocardiogram data to the trained machine learning model in step S240.

Figure 5:
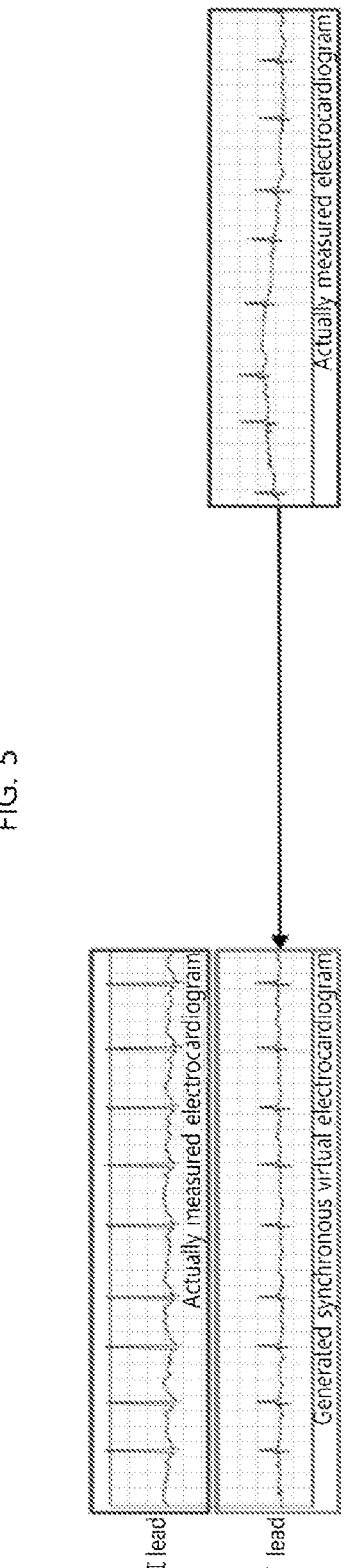
FIG. 5 is an example diagram illustrating step S240 shown in FIG. 2.

FIG. 5 is an example diagram illustrating step S240 shown in FIG. 2.

As shown in FIG. 5, it is assumed that the electrocardiogram acquisition unit 130 has acquired a V1-lead electrocardiogram. Then, the electrocardiogram generation unit 140 generates a V2 style electrocardiogram from the input lead electrocardiogram by inputting the V1-lead electrocardiogram to the machine learning model trained using V2-lead electrocardiogram data.

Figure 6:
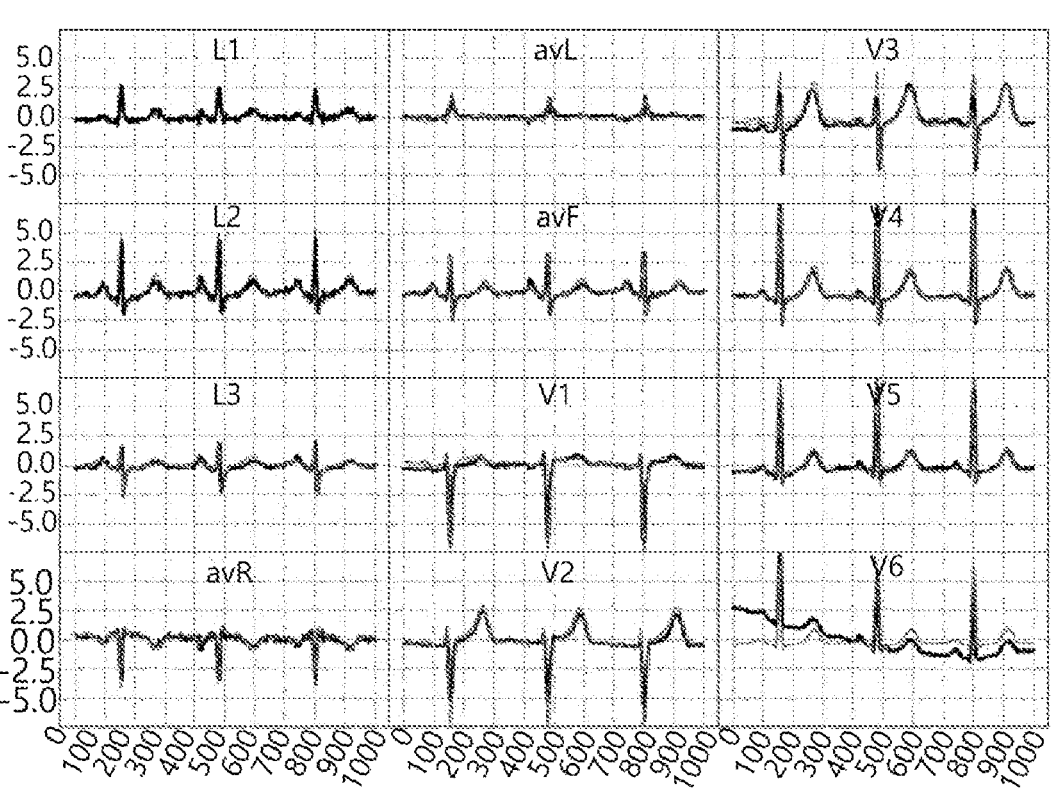
FIG. 6 is an example diagram illustrating electrocardiogram data generated in step S240 shown in FIG. 2.

FIG. 6 is an example diagram illustrating electrocardiogram data generated in step S240 shown in FIG. 2.

As shown in FIG. 6, the thick lines denote actual electrocardiograms, and the thin lines denote the results obtained by generating electrocardiograms based on styles.

As described above, the synchronous electrocardiogram generation apparatus 100 according to an embodiment of the present invention identifies the style of the electrocardiogram, determines which type of electrocardiogram the currently input electrocardiogram data is, and generates a plurality of virtual synchronous lead electrocardiograms expected to have been measured at the same time synchronized according to each style.

As described above, according to the present invention, synchronous electrocardiogram information is generated from two pieces of lead asynchronous electrocardiogram information using a deep learning algorithm, so that there can be provided highly accurate electrocardiograms that are not influenced by the age, gender, disease status, and attachment locations of electrodes of a measurement subject.

While the present invention has been described with reference to the embodiments shown in the drawings, these are merely examples. It will be understood by those skilled in the art that various modifications and other equivalent embodiments may be made therefrom. Therefore, the true technical protection range of the present invention should be determined by the technical spirit of the following patent claims.

The invention claimed is:

1. A method of generating synchronous electrocardiograms using a synchronous electrocardiogram generation apparatus, the method comprising:

collecting electrocardiogram data of a plurality of patients from a server operated by a hospital, and classifying the collected electrocardiogram data by style;

constructing a deep learning algorithm, and training a constructed machine learning model on styles of electrocardiograms by inputting the classified electrocardiogram data into the constructed machine learning model;

acquiring two lead electrocardiograms, measured at different times, using electrodes installed on a body of a measurement subject; and generating a plurality of virtual synchronous lead electrocardiograms by inputting the lead electrocardiograms of the measurement subject to the trained machine learning model.

2. The method of claim 1, wherein the classifying the collected electrocardiogram data by style includes classifying a plurality of the collected electrocardiogram data by at least one style among gender, age, disease status, attachment positions of electrodes, waveform characteristics, waveform curves, and noise signals of each patient.

3. The method of claim 2, wherein the training a constructed machine learning model on styles of electrocardiograms includes training the machine learning model on correlations between a plurality of electrocardiogram data and electrocardiogram styles by inputting the plurality of electrocardiogram data and the electrocardiogram styles to the machine learning model.

4. The method of claim 3, wherein the training a constructed machine learning model on styles of electrocardiograms includes constructing 12 machine learning models to perform training on styles for 12 standard electrocardiograms.

5. The method of claim 4, wherein the 12 machine learning models are constructed using one principle selected between an autoencoder and a generative adversarial network or are constructed using a mixture of the two principles.

6. The method of claim 4, wherein the generating a plurality of virtual synchronous lead electrocardiograms includes generating 12 pieces of electrocardiogram data changed into each style by inputting the lead electrocardiograms of the measurement subject into the 12 machine learning models.

7. The method of claim 5, wherein the generative adversarial network comprises a generator and a discriminator, and wherein the generator is configured to generate synthetic electrocardiogram data by inputting randomly generated variables, and the discriminator is configured to classify synthetic electrocardiogram data and real data as either generated or real.

8. The method of claim 5, wherein the autoencoder comprises an encoder configured to express potential characteristics of data and a decoder configured to restore corresponding expressions to original data.

9. The method of claim 1, wherein generating a plurality of virtual synchronous lead electrocardiograms comprises generating a lead I style electrocardiogram from at least one of the two lead electrocardiograms.

10. The method of claim 1, wherein the electrodes installed on the body of the measurement subject comprise electrodes of a 1-lead electrocardiogram smart watch device.

11. A method of generating synchronous electrocardiograms, the method comprising:

obtaining, from a server, a plurality of electrocardiogram signals corresponding to a plurality of patients;

classifying, each electrocardiogram signal of the plurality of electrocardiogram signals as one of a plurality of types corresponding to different patient-specific parameters and/or waveform characteristics to obtain classified electrocardiogram data;

training a machine learning model on the plurality of types of electrocardiogram signals using the classified electrocardiogram data;

obtaining a first lead electrocardiogram and a second lead electrocardiogram measured using electrodes installed on a subject, wherein the second lead electrocardiogram is measured at a different time than a time at which the first lead electrocardiogram is measured; and generating a plurality of virtual synchronous lead electrocardiograms by inputting the first lead electrocardiogram and the second lead electrocardiogram into the machine learning model.

12. The method of claim 11, wherein the patient-specific parameters and/or waveform characteristics include one or more of gender, age, disease status, attachment positions of electrodes, waveform characteristics, waveform curves, or noise signals of each patient.

13. The method of claim 12, wherein training the machine learning model includes training the machine learning model on correlations between a plurality of electrocardiogram data and electrocardiogram types by inputting the plurality of electrocardiogram data and the plurality of types to the machine learning model.

14. The method of claim 13, wherein training the machine learning model includes (i) constructing twelve machine learning models for generating twelve standard electrocardiograms and (ii) training each of the twelve machine learning models on electrocardiogram data of the plurality of types.

15. The method of claim 14, wherein one or more of the twelve machine learning models are constructed using an autoencoder or a generative adversarial network or both.

16. The method of claim 14, wherein generating the plurality of virtual synchronous lead electrocardiograms includes generating twelve electrocardiogram signals matching an identified type of the plurality of types based on the first lead electrocardiogram and the second lead electrocardiogram by inputting the first lead electrocardiogram and the second lead electrocardiogram of the subject into the twelve machine learning models.

17. The method of claim 15, wherein the generative adversarial network comprises a generator and a discriminator, and wherein the generator is configured to generate synthetic electrocardiogram data by inputting randomly generated variables, and the discriminator is configured to classify synthetic electrocardiogram data and real data as either generated or real.

18. The method of claim 15, wherein the autoencoder comprises an encoder configured to express potential characteristics of data and a decoder configured to restore corresponding expressions to original data.

19. The method of claim 11, wherein generating the plurality of virtual synchronous lead electrocardiograms comprises generating a lead I type electrocardiogram from the first lead electrocardiogram and the second lead electrocardiogram.

20. The method of claim 11, wherein the electrodes installed on the subject comprise electrodes of a 1-lead electrocardiogram smart watch device.

* * * * *